United States Patent [19]
Olesen et al.

[11] Patent Number: 5,945,417
[45] Date of Patent: Aug. 31, 1999

[54] HETEROCYCLIC COMPOUNDS, THEIR PREPARATION AND USE

[75] Inventors: Preben Houlberg Olesen, Copenhagen; Anders Kanstrup, Espergærde, both of Denmark

[73] Assignee: Novo Nordisk, Bagsvaerd, Denmark

[21] Appl. No.: 09/000,112

[22] PCT Filed: Jul. 31, 1996

[86] PCT No.: PCT/DR96/00331

§ 371 Date: Jan. 21, 1998

§ 102(e) Date: Jan. 21, 1998

[87] PCT Pub. No.: WO97/05137

PCT Pub. Date: Feb. 13, 1997

[30] Foreign Application Priority Data

Jul. 31, 1995 [DK] Denmark ................ 0868/95

[51] Int. Cl.[6] .............. A61K 31/535; A61K 31/44; C07D 413/04; C07D 471/04
[52] U.S. Cl. .................. 514/232.8; 514/228.2; 514/254; 514/292; 544/60; 544/126; 544/361; 546/87
[58] Field of Search .............. 546/87; 544/126, 544/60, 361; 514/292, 232.8, 254, 228.2

[56] References Cited

U.S. PATENT DOCUMENTS 4,952,584  8/1990  Thompson et al. ............ 514/292
5,536,721  7/1996  Jakobsen ..................... 514/232.8

FOREIGN PATENT DOCUMENTS 1268772  3/1972  United Kingdom .

OTHER PUBLICATIONS

Blackburn et al., "(+)11–Amino–2,6–Dimethyl–1,2,3,4–Tetrahydro–6H Quinindolin–1–One, A Novel GABA$_A$ Modulator With Potential Anxiolytic Activity", Bioorganic & Medicinal Chemistry Letters, vol. 4, No. 2., pp. 279–284.

Bolton et al., "Synthesis And Potential Anxiolytic Activity of 4—Amino–Pyrido[2,3–b]Indoles", Bioorganic & Medicinal Chemistry Letters, vol. 3, No. 10, pp. 1941–1946, 1993.

Knopfel T et al. J. Med. Chem. 38(9), pp. 1417–1426, Apr. 1995.

*Primary Examiner*—Evelyn Mei Huang
*Attorney, Agent, or Firm*—Steve T. Zelson; Carol E. Rozek

[57] ABSTRACT

The present invention relates to a method of treating a disease in the central nervous system via the metabotropic glutamate receptor system, the use of the known as well as novel pyridino(2,3-b) indoles (formula Ib) for the preparation of a medicament for treating said diseases, novel therapeutic active pyridino(2,3-b) indoles, a method for preparing the same and pharmaceutical compositions comprising these compounds.

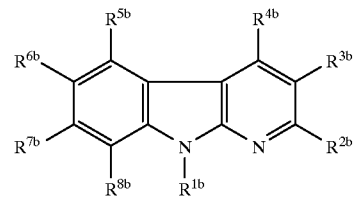

(Ib)

28 Claims, No Drawings

HETEROCYCLIC COMPOUNDS, THEIR PREPARATION AND USE

CROSS-REFERENCE TO RELATED APPLICATIONS

This application is a 35 U.S.C. 371 national application of PCT/DK96/00331 filed Jul. 31, 1996 published as WO 97/05137 on Feb. 13, 1997 and claims priority under 35 U.S.C. 119 of Danish application 0868/95 filed Jul. 31, 1995, the contents of which are fully incorporated herein by reference.

The present invention relates to a method of treating a disease in the central nervous system via the metabotropic glutamate receptor system, the use of known as well as new pyridino[2,3-b]indoles for the preparation of a medicament for treating said diseases, novel therapeutic active pyridino [2,3-b]indoles, a method for preparing the same and pharmaceutical compositions comprising these compounds.

Recent molecular biological studies have clearly established the existence of two major types of glutamate receptors in the central nervous system namely the ionotropic and the metabotropic glutamate receptors. The latter is characterised by being G-protein-linked to changes in second messenger formation and modulation of ion channel function, (Meldrum, B. (1991) Epilepsy Res. 10, 55–61, Chapman, A. (1991) in Excitatory Amino Acids p. 265–286, Blackwell scientific publ. ltd., Oxford).

At present 8 different subtypes of the metabotropic glutamate receptors are described ($MGluR_1$ to $MGluR_8$) and in addition some spliced variants of the subtypes are reported.

The Metabotropic glutamate receptor subtypes $MGluR_1$ and $MGluR_5$ are coupled to phosphoinositide hydrolysis (Johnson, G. and Bigge, C. F. (1991) Annu. Rep. Med. Chem. 26, 11–22, Hansen, J. J. and Krogsgaard Larsen, P. Med. Res. Rev. 10,55–94, Thomsen, C. and Suzdak, P. (1993) Eur. J. Pharmacol. 245 ,299), while the others are coupled to cyclic AMP formation (Schoepp, D. D., Johnson, B. G. and Monn, J. A. (1992) J. Neurochem. 58, 1184–1186, Cartmell et al. (1992) J. Neurochem. 58, 1964–1966, Manzoni, O. et al. (1992) Eur. J. Pharmacol. 225, 357–358).

Compounds such as L-glutamate, quisqualate and ibotenate are known to act as non-selective agonists on the metabotropic glutamate receptors, while selective ionotropic glutamate receptor agonists such as NMDA, AMPA and kainate have little effect on these receptors.

Recently a few compounds without activity at the ionotropic glutamate receptors but with activity at the metabotropic receptors have been identified.

These comprise trans-ACPD (trans 1S,3R-1-aminocyclopentane-1,3-dicarboxylic acid), the partial agonist L-AP3 (L-2-amino-3-phosphonopropionic acid) (Palmer, E., Monaghan, D. T. and Cotman, C. W. (1989) Eur. J. Pharmacol. 166, 585–587, Desai, M. A. and Conn, P. J. (1990) Neurosci. Lett. 109, 157–162, Schoepp, D. D. et al. (1991), J. Neurochem. 56, 1789–1796, Schoepp D. D. and Johnson B. G. (1989), J. Neurochem. 53,1865–1613), L-AP4 (L-2-amino4-phosphonobutyrate) which is an agonist at the $MGluR_4$ receptor (Thomsen C. et al. (1992), Eur. J. Pharmacol. 227, 361–362) and some of the isomers of CCG (2-(carboxycyclopropyl)glycines) especially L-CCG-I and L-CCG-II (Hayashi, Y. et al. (1992), Br. J. Pharmacol. 107, 539–543).

Very few selective antagonists at the metabotropic glutamate receptors have been reported, however some phenylglycine derivatives S-4CPG (S-4-carboxyphenyl glycine), S-4C3HPG (S-4-carboxy-3-hydroxyphenyl glycine) and S-MCPG (S-alpha methyl4-carboxyphenyl glycine) have been reported to antagonise trans ACPD stimulated phosphoinositide hydrolysis and thus possibly acting as antagonists at the metabotropic glutamate receptors at the subtypes $MGluR_1$ and $MGluR_5$ (Thomsen, C. and Suzdak, P, (1993) Eur. J. Pharmacol. 245, 299).

Literature evidence suggests that compounds selective for the metabotropic glutamate receptors either as agonists or antagonists are useful in the treatment of different neurological diseases.

The use of compounds active at the metabotropic glutamate receptors for the treatment of epilepsy is corroborated by investigations of the influence of trans-ACPD in the formation of convulsions (Sacaan and Schoepp, (1992), Neurosci. lett. 139, 77) and that phosphoinositide hydrolysis mediated via MGluR is increased after kindling experiments in rats (Akiyama et al. (1992),Brain Res. 569, 71).

Trans-ACPD has been shown to increase release of dopamine in the rat brain which indicates that compounds acting on the metabotropic glutamate receptors might be usable for the treatment of Parkinson's disease and Huntington's Chorea (Sacaan et al. (1992), J. Neurochem. 59, 245).

The use of compounds active at the metabotropic glutamate receptors for treatment of neurological diseases such as senile dementia has been indicated by the findings of Zheng and Gallagher ((1992), Neuron 9, 163) and Bashir et al. ((1993), Nature 363, 347) who demonstrated that activation of metabotropic glutamate receptors are necessary for the induction of long term potentiation (LTP) in nerve cells (septal nucleus,hippocampus) and the finding that long term depression is induced after activation of metabotropic glutamate receptors in cerebellar granule cells (Linden et al. (1991), Neuron 7,81).

Investigations also show that in the treatment of deficiencies of mental and motoric performance seen after conditions of brain ischemia the metabotropic glutamate receptor active compounds may prove usable.

Trans-ACPD has been shown to be a neuroprotective agent in an MCAO model in mice (Chiamulera et al. (1992), Eur. J. Pharmacol. 215, 353), and it has been shown to inhibit NMDA induced neurotoxicity in nerve cell cultures (Koh et al., (1991), Proc. Natl. Acad. Sci. USA 88, 9431).

Also in the treatment of pain the metabotropic glutamate receptor active compounds seem of interest, proved by the fact that antagonists at the metabotropic glutamate receptors antagonises sensory synaptic response to noxious stimuli of thalamic neurons (Eaton, S. A. et al. (1993), Eur. J. Neurosci. 5, 186).

The above findings support that compounds acting on the metabotropic glutamate receptors are useful for the treatment of epilepsy, neurological diseases such as senile dementia, Parkinson's disease, Huntington's Chorea, pain and deficiencies of mental and motoric performance seen after conditions of brain ischemia.

We have now discovered that a series of pyridino[2,3-b] indoles, some of which compounds are known from GB 1 268 772 (Glaxo Laboratories Ltd.) to possess antiviral activity, are potent antagonists at the metabotropic glutamate receptors.

Thus the present invention is concerned with a method of treating a disease in the central nervous system via the metabotropic glutamate receptor system comprising administering to a subject in need thereof an effective amount of a compound of formula Ib

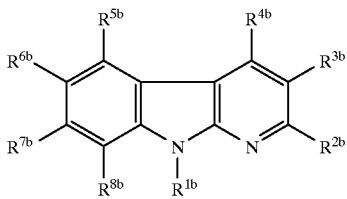

(Ib)

wherein $R^{1b}$ is H; $C_{1-6}$-alkyl optionally substituted with halogen; $C_{2-6}$-alkenyl; $C_{2-6}$-alkynyl; $C_{3-6}$-cycloalkyl; $C_{1-6}$-alkyl substituted with $C_{3-6}$-cycloalkyl; carboxy; —$COR^{9b}$; —$COOR^{9b}$; $C_{1-6}$-alkyl substituted with dimethylamino; —$R^{9b}$—O—$R^{10b}$; —$R^{9b}$—O—$R^{10b}$—O—$R^{11b}$; phenylsulfonyl; benzoyl; benzyl or phenyl each of which aromatic group is optionally substituted with $C_{1-6}$-alkyl, $C_{1-6}$-alkoxy, halogen, carboxy or nitro; wherein $R^{9b}$, $R^{10b}$, $R^{11b}$ and are independently $C_{1-6}$-alkyl;

$R^{2b}$ is amino optionally substituted with one or two $C_{1-6}$-alkyl which alkyl group(s) is/are optionally substituted with hydroxy, morpholino, amino unsubstituted or mono or disubstituted with $C_{1-6}$-alkyl, phenyl, phenylsulfonyl or benzyl; piperidino; morpholino; or piperazino optionally N-substituted with $C_{1-6}$-alkyl;

$R^{3b}$ is H; carboxy; cyano; nitro; $C_{1-6}$-alkyl optionally substituted with hydroxy; —$R^{9b}$—O—$R^{10b}$; —$COOR^{9b}$; wherein $R^{9b}$ and $R^{10b}$ are as defined above; morpholinocarbonyl; thiomorpholinocarbonyl; piperazinylcarbonyl optionally substituted with $C_{1-6}$-alkyl; tetrazolyl; oxadiazolyl or thiadiazolyl optionally substituted with $C_{1-6}$-alkyl or $C_{3-6}$-cycloalkyl; morpholinomethyl; amino unsubstituted or mono or disubstituted with $C_{1-6}$-alkyl; methylamino unsubstituted or N-mono or disubstituted with $C_{1-6}$-alkyl; sulfamoyl unsubstituted or mono or disubstituted with $C_{1-6}$-alkyl; or carbamoyl unsubstituted or mono or disubstituted with $C_{1-6}$-alkyl which alkyl group(s) is/are optionally substituted with dimethylaminomethyl, halogen, phenyl or benzyl;

$R^{4b}$ is H; or $C_{1-6}$-alkyl;

$R^{5b}$, $R^{6b}$, $R^{7b}$, and $R^{8b}$ are independently H; nitro; amino; halogen; trifluoromethyl; trifluoroacetyl; sulfo; carboxy; carbamoyl; sulfamoyl; —$COR^{9b}$; —$COOR^{9b}$; wherein $R^{9b}$ is as defined above; $C_{1-6}$-alkoxy; or $C_{1-6}$-alkyl optionally substituted with halogen;

or a salt thereof with a pharmaceutically acceptable acid or base.

These salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "$C_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec.butyl, isobutyl, tert.butyl, n-pentyl, 2-methylbutyl, 3-methylbutyl, n-hexyl, 4-methylpentyl, neopentyl, n-hexyl and 2,2-dimethylpropyl.

The term "$C_{1-6}$-alkoxy" as used herein, alone or in combination, refers to a monovalent substituent comprising a lower alkyl group linked through an ether oxygen having its free valence bond from the ether oxygen and having 1 to 6 carbon atoms e.g. methoxy, ethoxy, propoxy, butoxy, pentoxy.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term "$C_{3-6}$-cycloalkyl" as used herein refers to a radical of a saturated cyclic hydrocarbon with the indicated number of carbons such as cyclopropyl, cyclobutyl, cyclopentyl, or cyclohexyl.

The term "$C_{2-6}$-alkynyl" as used herein refers to unsaturated hydrocarbons which contain triple bonds, such as e.g. —C≡CH, —C≡CCH$_3$, —CH$_2$C≡CH, —CH$_2$CH$_2$C≡CH, —CH(CH$_3$)C≡H, and the like.

The term "halogen" means fluorine, chlorine, bromine and iodine.

It is to be understood that the invention extends to the use of each of the stereoisomeric forms of the compounds of formula Ib as well as the racemates.

In the method of the present invention, $R^{1b}$ is preferably benzyl optionally substituted with $C_{1-6}$-alkyl, $C_{1-6}$-alkoxy, halogen, carboxy or nitro, more preferably benzyl optionally substituted with halogen; $R^{2b}$ is preferably piperidino; morpholino; or piperazino optionally N-substituted with $C_{1-6}$-alkyl; more preferably morpholino; and $R^{3b}$ is preferably carboxy.

The present invention furthermore relates to the use of compounds of formula Ib for the preparation of a medicament for treatment of a disease in the central nervous system via the metabotropic glutamate receptor system.

In addition, the present invention is concerned with novel compounds of formula Ib

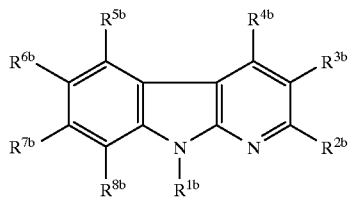

(Ib)

wherein $R^{1b}$ is benzyl optionally substituted with $C_{1-6}$-alkyl, $C_{1-6}$-alkoxy, halogen, carboxy or nitro, preferably benzyl optionally substituted with halogen;

$R^{2b}$ is piperidino; morpholino; or piperazino optionally N-substituted with $C_{1-6}$-alkyl; preferably morpholino;

$R^{3b}$ is H; carboxy; cyano; nitro; $C_{1-6}$-alkyl optionally substituted with hydroxy; —$R^{9b}$—O—$R^{10b}$; —$COOR^{9b}$; wherein $R^{9b}$ and $R^{10b}$ are as defined above; morpholinocarbonyl; thiomorpholinocarbonyl; piperazinylcarbonyl optionally substituted with $C_{1-6}$-alkyl; tetrazolyl; oxadiazolyl or thiadiazolyl optionally substituted with $C_{1-6}$-alkyl or $C_{3-6}$-cycloalkyl; morpholinomethyl; amino unsubstituted or mono or disubstituted with $C_{1-6}$-alkyl; methylamino unsubstituted or N-mono or disubstituted with $C_{1-6}$-alkyl; sulfamoyl unsubstituted or mono or disubstituted with $C_{1-6}$-alkyl; or carbamoyl unsubstituted or mono or disubstituted with $C_{1-6}$-alkyl which alkyl group(s) is/are optionally substituted with dimethylaminomethyl, halogen, phenyl or benzyl; preferably carboxy.

$R^{4b}$ is H; or $C_{1-6}$-alkyl;

$R^{5b}$, $R^{6b}$, $R^{7b}$, and $R^{8b}$ are independently H; nitro; amino; halogen; trifluoromethyl; trifluoroacetyl; sulfo; carboxy; carbamoyl; sulfamoyl; —$COR^{9b}$; —$COOR^{9b}$; wherein $R^{9b}$ is as defined above; $C_{1-6}$-alkoxy; or $C_{1-6}$-alkyl optionally substituted with halogen; or a salt thereof with a pharmaceutically acceptable acid or base.

Specific examples of compounds of the invention include the following:

Ethyl 9-benzyl-2-piperidinopyridino[2,3-b]indole-3-carboxylate,

Ethyl 9-benzyl-2-morpholinopyridino[2,3-b]indole-3-carboxylate,

9-Benzyl-2-morpholinopyridino[2,3-b]indole-3-carboxylic acid,

9-Benzyl-2-morpholinopyridino[2,3-b]indole,

9-Benzyl-2-piperidinopyridino[2,3-b]indole.

The compounds of formula Ib may e.g. be prepared in accordance with the teaching of GB 1 268 772. However, the invention also relates to an advantageous method of preparing the above mentioned compounds. This method comprises a) reacting a compound of formula IIb,

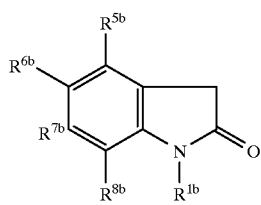

(IIb)

prepared by well known methods, wherein $R^{1b}$, $R^{5b}$, $R^{6b}$, $R^{7b}$ and $R^{8b}$ have the meanings defined above, with a N,N-dimethyl amide, preferably dimethylformamide or dimethylacetamide, and $POX_3$, wherein X is chlorine or bromine, using Vilsmeyer-Hack conditions, to form a compound of formula IIIb,

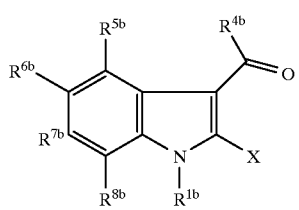

(IIIb)

wherein X is chlorine or bromine, and $R^{1b}$, $R^{4b}$, $R^{5b}$, $R^{6b}$, $R^{7b}$, and $R^{8b}$ have the meanings defined above; and subsequently b) reacting a compound of formula IIIb, wherein X is chlorine or bromine, and $R^{1b}$, $R^{4b}$, $R^{5b}$, $R^{6b}$, $R^{7b}$, and $R^{8b}$ have the meanings defined above, with a compound N≡C—$CH_2$-$Z^b$ wherein $Z^b$ is cyano, nitro, $COOR^{9b}$ wherein $R^{9b}$ have the meanings defined above, sulfamoyl unsubstituted or mono or disubstituted with $C_{1-6}$-alkyl, or carbamoyl unsubstituted or mono or disubstituted with $C_{1-6}$-alkyl; together with an amine as defined for $R^{2b}$, preferably morpholine or piperidine, either in the presence or absence of an added strong base, such as sodium hydride, to form a compound of formula IVb, wherein $Z^b$, $R^{1b}$, $R^{2b}$, $R^{4b}$, $R^{5b}$, $R^{6b}$, $R^{7b}$, and $R^{8b}$ have the meanings defined above, or

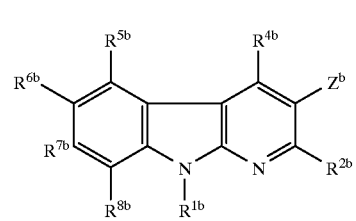

(IVb)

c) reacting a compound of formula IVb, wherein $Z^b$, $R^{1b}$, $R^{2b}$, $R^{4b}$, $R^{5b}$, $R^{6b}$, $R^{7b}$, and $R^{8b}$ have the meanings defined above, by means of well known chemical reactions transforming the $Z^b$ group to hydrogen or to other functional groups such as acids, esters, amides, amines, or reaction products thereof as described for $R^{3b}$, to form a compound of formula Ib, wherein $R^{1b}$, $R^{2b}$, $R^{3b}$, $R^{4b}$, $R^{5b}$, $R^{6b}$, $R^{7b}$, and $R^{8b}$ have the meanings defined above, or d) reacting a compound of formula formula Ib, wherein $R^{1b}$, $R^{2b}$, $R^{3b}$, and $R^{4b}$ have the meanings defined above, and at least one of $R^{5b}$, $R^{6b}$, $R^{7b}$, or $R^{8b}$ is H with well known reactive substrates leading to aromatic substitution using the reaction conditions known in the art, to form a compound of formula Ib, wherein $R^{5b}$, $R^{6b}$, $R^{7b}$, or $R^{8b}$ have the meanings defined above provided that at least one of $R^{5b}$, $R^{6b}$, $R^{7b}$, or $R^{8b}$ is not H, or e) a compound of formula Ib or formula IIb or formula IVb with different $R^{5b}$, $R^{6b}$, $R^{7b}$, or $R^{8b}$ could be prepared by using conventional organic chemistry on functional groups already introduced as $R^{5b}$, $R^{6b}$, $R^{7b}$, or $R^{8b}$ groups.

The pharmacological properties of the compounds of the invention can be illustrated by determining their effects in different conventional radioligand binding assays or in functional in vitro assays.

The compounds of the invention were studied in an in vitro assay for measuring inhibition of Pi-hydrolysis in BHK 570 cells expressing $mGluR_1\alpha$ receptors.

Principle

The metabotropic glutamate receptor (mGluR) is selectively activated by trans-aminocyclopentane dicarboxylic acid and is coupled to the hydrolysis of inositol phosphates via a GTP-binding protein. At the molecular level, cDNAs encoding six subtypes of the mGluR family have been isolated. The first subtype isolated (Houamed et al., 1991, Science 252, 1318), termed the mGluR1α, has been shown to be coupled to Pl-hydrolysis when expressed in baby hamster kidney cells (BHK) (Thomsen et al., Brain Res. (in press)). In these cells no stimulation by 1 mM quisqualate or glutamate was observed with control BHK cells whereas a 6–8 fold increase over basal Pl-hydrolysis was seen with BHK cells expressing mGluR1α.

Cell Culture

BHK570 cells expressing mGluR1α are cultured in DMEM (4.5 g/l glucose, 2 mM glutamin); 5% foetal calf serum; 0.10 mg/ml neomycin; 0.5 mg/ml G418; 1 $\mu$M methotrexate; 50 $\mu$g/ml gentamycin. Cells are subcultured every 5 days using 0.05% trypsin/EDTA in PBS.

Inositol Phosphate Formation

The protocol for PI-hydrolysis was measured using a modification of a method previously described (Berridge et al., 1982, Biochem. J. 206,587). Cells were plated in 16 mm wells (24 well multidish, Costar) with 1 confluent 100 mm dish per multidish. Replace the medium 24 h before the experiment with 500 $\mu$l fresh growth medium containing 4 $\mu$Ci/ml myo-[2-$^3$H]inositol (specific activity 18 Ci/mmol, Amersham). The cells were washed twice with Krebs-Henseleit buffer (Sigma cat. #3753: glucose 2.0 g/l, $MgSO_4$ 0.141 g/l, $KHPO_4$ 0.16 g/l, KCl 0.35 g/l, NaCl 6.90 g/l and $NaHCO_3$ 2.1 g/l) supplemented with 10 mM LiCl and 2.5 mM $CaCl_2$. The buffer was equilibrated with 5% $CO_2$, 95% air to pH 7.5 at 37° C. Following 5 min of preincubation in the above buffer, buffer or test compounds were added and cells were incubated for 30 min at 37° C. In antagonist studies, add test compounds 5 min prior to agonist stimulation. PI-formation was stopped by placing the cells on ice and quickly aspirating the media. The wells were washed once with ice-cold Krebs-Henseleit buffer and subsequently 1 ml ice-cold 10% perchloric acid was added to each well. Place the cells on ice for 20 min. In Nunc minisorp test tubes (75×12 mm, cat. #443990): add 250 $\mu$l of 10 mM EDTA, pH 7.0 +5% Universal Indicator (Merck). Transfer the PCA extract to each tube containing the pH-indicator. Neutralize the samples with 1.5 M KOH+60 mM HEPES to pH 7.5 (~1100–1200 $\mu$l). Centrifugate (6.000 rpm, 5 min, 0° C.). They can be stored frozen at this point. Fractions of inositolphosphates were separated using ion-exchange columns (Amersham, RPN 1908) according to the method provided by Amersham.

Separation of inositol phoshates on ion-exchange columns

Prepare columns with 5 ml 1 M $KHCO_3$ and wash with 15 ml dist. water. Adjust vacuum so that the flow-rate does not exceed 5 ml/min. Add 4 ml dist. water and subsequently 1 ml [$^3$H]InsP sample. Wash with 5 ml dist. water. IP1 to IP4 fractions may be collected with 5 ml 0.05; 0.10; 0.17 and 0.25 M $KHCO_3$, respectively. Usually IP1 and IP2 fractions are collected simultaneously. Scintillation liquid: use 12–15 ml Ultima Gold (Packard).

Testprocedure

Testcompounds are dissolved in DMSO, DMSO and Pluronic F-127 or ethanol and diluted in assay buffer. Glutamate (10 $\mu$M and 1000 $\mu$M) and buffer alone are included as a control.

Results

The stimulation by 10 $\mu$M shall represent a submaximal stimulation. The response by 10 $\mu$M glutamate should exceed 3-fold the basal level and should be below maximal stimulation (glutamate at 1 mM). The results are calculated relative to the stimulation by 10 $\mu$M glutamate and a dose response curve is generated.

An example of a test result obtained by testing a compound of the present invention in the above mentioned assay appear from the following Table 1.

TABLE 1

| Compound No. | $IC_{50}$ ($\mu$M) |
|---|---|
| 3 | 10 |

The compounds according to the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from a disease in the central nervous system related to the metabotropic glutamate receptor system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula Ib or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers andlor coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

The invention will now be described in further detail with reference to the following examples.

EXAMPLE 1b

Ethyl 9-benzyl-2-piperidinopyridino[2,3-b]indole-3-carboxylate (1b)

To a slurry of 1.35 g of 1-benzyl-2-chloroindole-3-carbaldehyde in 30 ml abs. EtOH was added 1 ml of ethyl cyanoacetate and 3.5 ml of piperidine, and the mixture was stirred at room temperature for 2.5 days. 30 ml of ice/water was added, and the precipitate was isolated by filtration and dried to give (1b). Yield 1.6 g of (1b), m.p. 155–156° C.

EXAMPLE 2b

Ethyl 9-benzyl-2-morpholinopyridino[2,3-b]indole-3-carboxylate (2b)

To a slurry of 1.35 g of 1-benzyl-2-chloroindole-3-carbaldehyde in 30 ml abs. EtOH was added 1.5 ml of ethyl cyanoacetate and 3.5 ml of morpholine, and the mixture was stirred at room temperature for 2 days. The mixture was then heated to reflux for 5 hours, cooled to room temperature and filtered to give (2b). Yield 1.6 g of (2b), m.p. 151–152° C.

EXAMPLE 3b

9-Benzyl-2-morpholinopyridino[2,3-b]indole-3-carboxylic acid (3b)

1.3 g of (2b) was covered with a solution of 200 mg of KOH in 2 ml of water, and stirred at room temperature for 1 hour and at 60° C. for 2 hours. After cooling the solvent was evaporated and the product precipitated with water and acetic acid to give 1.1 g of a mixture of 2 compounds. These two products were separated by column chromatography, on Silica 60 using methanol and methylenedichloride 1+9 as the eluent, to give (3b). Yield 480 mg of (3b). An analytical sample was recrystallized from EtOH, m.p. 282–287° C.

We claim:

1. A method of treating a disease in the central nervous system via the metabotropic glutamate receptor system comprising administering to a subject in need thereof an effective amount of a compound of formula Ib

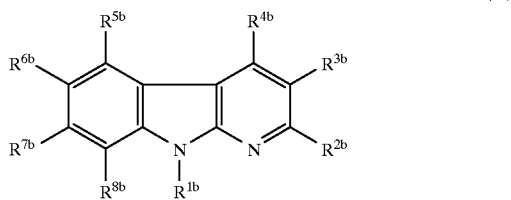

(Ib)

wherein $R^{1b}$ is H; $C_{1-6}$-alkyl optionally substituted with halogen; $C_{2-6}$-alkenyl; $C_{2-6}$-alkynyl; $C_{3-6}$-cycloalkyl; $C_{1-6}$-alkyl substituted with $C_{3-6}$-cycloalkyl; carboxy; —$COR^{9b}$; —$COOR^{9b}$; $C_{1-6}$-alkyl substituted with dimethylamino; —$R^{9b}$—O—$R^{10b}$; —$R^{9b}$—O—$R^{10b}$—O—$R^{11b}$; phenylsulfonyl; benzoyl; benzyl or phenyl each of which aromatic group is optionally substituted with $C_{1-6}$-alkyl, $C_{1-6}$-alkoxy, halogen, carboxy or nitro; wherein $R^{9b}$, $R^{10b}$ and $R^{11b}$ are independently $C_{1-6}$-alkyl;

$R^{2b}$ is amino optionally substituted with one or two $C_{1-6}$-alkyl which alkyl group(s) is/are optionally substituted with hydroxy, morpholino, amino unsubstituted or mono- or disubstituted with $C_{1-6}$-alkyl, phenyl, phenylsulfonyl or benzyl; piperidino; morpholino; or piperazino optionally N-substituted with $C_{1-6}$-alkyl;

$R^{3b}$ is H; carboxy; cyano; nitro; $C_{1-6}$-alkyl optionally substituted with hydroxy; —$R^{9b}$—O—$R^{10b}$; —$COOR^{9b}$; wherein $R^{9b}$ and $R^{10b}$ are independently $C_{1-6}$-alkyl; morpholinocarbonyl; thiomorpholinocarbonyl; piperazinylcarbonyl optionally substituted with $C_{1-6}$-alkyl; tetrazolyl; oxadiazolyl or thiadiazolyl optionally substituted with $C_{1-6}$-alkyl or $C_{3-6}$-cycloalkyl; morpholinomethyl; amino unsubstituted or mono- or disubstituted with $C_{1-6}$-alkyl; methylamino unsubstituted or N-mono- or disubstituted with $C_{1-6}$-alkyl; sulfamoyl unsubstituted or mono- or disubstituted with $C_{1-6}$-alkyl; or carbamoyl unsubstituted or mono- or disubstituted with $C_{1-6}$-alkyl which alkyl group(s) is/are optionally substituted with dimethylaminomethyl, halogen, phenyl or benzyl;

$R^{4b}$ is H; or $C_{1-6}$-alkyl;

$R^{5b}$, $R^{6b}$, $R^{7b}$, and $R^{8b}$ are independently H; nitro; amino; halogen; trifluoromethyl; trifluoroacetyl; sulfo; carboxy; carbamoyl; sulfamoyl; —$COR^{9b}$; —$COOR^{9b}$; wherein $R^{9b}$ is $C_{1-6}$-alkyl; $C_{1-6}$-alkoxy; or $C_{1-6}$-alkyl optionally substituted with halogen; or a salt thereof with a pharmaceutically acceptable acid or base.

2. A method according to claim 1 wherein $R^{1b}$ is benzyl optionally substituted with $C_{1-6}$-alkyl, $C_{1-6}$-alkoxy, halogen, carboxy or nitro.

3. A method according to claim 2 wherein $R^{1b}$ is benzyl optionally substituted with halogen.

4. A method according to claim 1 wherein $R^{2b}$ is piperidino; morpholino; or piperazino optionally N-substituted with $C_{1-6}$-alkyl.

5. A method according to claim 4 wherein $R^{2b}$ is morpholino.

6. A method according to claim 1 wherein $R^{3b}$ is carboxy.

7. A method according to claim 1 wherein the compound of formula Ib is selected from the group consisting of:

Ethyl 9-benzyl-2-piperidinopyridino[2,3-b]indole-3-carboxylate,

Ethyl 9-benzyl-2-morpholinopyridino[2,3-b]indole-3-carboxylate,

9-Benzyl-2-morpholinopyridino[2,3-b]indole-3-carboxylic acid,

9-Benzyl-2-morpholinopyridino[2,3-b]indole,

9-Benzyl-2-piperidinopyridino[2,3-b]indole.

8. A method according to claim 1 wherein the disease is epilepsy, senile dementia, Parkinson's disease, Huntington's Chorea, pain or deficiencies of mental and motoric performance seen after conditions of brain ischemia.

9. A compound of formula Ib

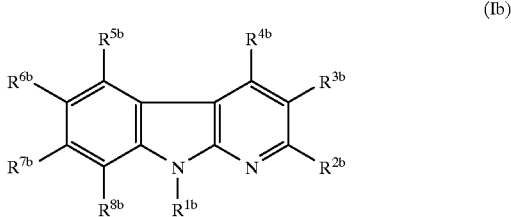

(Ib)

wherein $R^{1b}$ is benzyl optionally substituted with $C_{1-6}$-alkyl, $C_{1-6}$-alkoxy, halogen, carboxy or nitro;

$R^{2b}$ is piperidino; morpholino; or piperazino optionally N-substituted with $C_{1-6}$-alkyl;

$R^{3b}$ is; carboxy; cyano; nitro; $C_{1-6}$-alkyl optionally substituted with hydroxy; —$R^{9b}$—O—$R^{10b}$; —$COOR^{9b}$; wherein $R^{9b}$ and $R^{10b}$ are independently $C_{1-6}$-alkyl; morpholinocarbonyl; thiomorpholinocarbonyl; piperazinylcarbonyl optionally substituted with $C_{1-6}$-alkyl; tetrazolyl; oxadiazolyl or thiadiazolyl optionally substituted with $C_{1-6}$-alkyl or $C_{3-6}$-cycloalkyl; morpholinomethyl; amino unsubstituted or mono- or disubstituted with $C_{1-6}$-alkyl; methylamino unsubstituted or N-mono- or disubstituted with $C_{1-6}$-alkyl; sulfamoyl unsubstituted or mono- or disubstituted with $C_{1-6}$-alkyl; or carbamoyl unsubstituted or mono- or disubstituted with $C_{1-6}$-alkyl which alkyl group(s) is/are optionally substituted with dimethylaminomethyl, halogen, phenyl or benzyl;

$R^{4b}$ is H; or $C_{1-6}$-alkyl;

$R^{5b}$, $R^{6b}$, $R^{7b}$, and $R^{8b}$ are independently H; nitro; amino; halogen; trifluoromethyl; trifluoroacetyl; sulfo; carboxy; carbamoyl; sulfamoyl; —$COR^{9b}$; —$COOR^{9b}$; wherein $R^{9b}$ is $C_{1-6}$-alkyl; $C_{1-6}$-alkoxy; or $C_{1-6}$-alkyl optionally substituted with halogen; or a salt thereof with a pharmaceutically acceptable acid or base.

10. A compound according to claim 9 wherein $R^{1b}$ is benzyl optionally substituted with halogen.

11. A compound according to claim 9 wherein $R^{2b}$ is morpholino.

12. A compound according to claim 9 wherein $R^{3b}$ is carboxy.

13. A compound according to claim 10 wherein $R^{2b}$ is morpholino.

14. A compound according to claim 10 wherein $R^{3b}$ is carboxy.

15. A compound according to claim 11 wherein $R^{3b}$ is carboxy.

16. A compound according to claim 9 wherein $R^{1b}$ is benzyl, $R^{2b}$ is morpholino, and $R^{3b}$ is carboxy.

17. A compound according to claim 13 wherein $R^{5b}$, $R^{6b}$, $R^{7b}$ and $R^{8b}$ are hydrogen.

18. A compound according to claim 14 wherein $R^{5b}$, $R^{6b}$, $R^{7b}$ and $R^{8b}$ are hydrogen.

19. A compound according to claim 15 wherein $R^{5b}$, $R^{6b}$, $R^{7b}$ and $R^{8b}$ are hydrogen.

20. A compound according to claim 16 wherein $R^{5b}$, $R^{6b}$, $R^{7b}$ and $R^{8b}$ are hydrogen.

21. A compound according to claim 9 wherein $R^{1b}$ is ethylbenzyl, $R^{2b}$ is piperidino, and $R^{3b}$ is carboxylate, and $R^{4b}$, $R^{5b}$, $R^{6b}$, $R^{7b}$, $R^{8b}$ are hydrogen.

22. A compound according to claim 9 wherein $R^{1b}$ is ethylbenzyl, $R^{2b}$ is morpholino, and $R^{3b}$ is carboxylate and $R^{4b}$, $R^{5b}$, $R^{6b}$, $R^{7b}$ and $R^{8b}$ are hydrogen.

23. A compound according to claim 9 wherein $R^{1b}$ is benzyl, $R^{2b}$ is morpholino, and $R^{3b}$ is carboxylate and $R^{4b}$, $R^{5b}$, $R^{6b}$, $R^{7b}$ and $R^{8b}$ are hydrogen.

24. A compound according to claim 9 wherein $R^{1b}$ is benzyl, $R^{2b}$ is morpholino, and $R^{4b}$, $R^{5b}$, $R^{6b}$, $R^{7b}$ and $R^{8b}$ are hydrogen.

25. A compound according to claim 9 wherein $R^{1b}$ is benzyl, $R^{2b}$ is piperidino, and $R^{4b}$, $R^{5b}$, $R^{6b}$, $R^{7b}$ and $R^{8b}$ are hydrogen.

26. A pharmaceutical composition comprising a compound according to claim 9 together with a pharmaceutically acceptable carrier or diluent.

27. The pharmaceutical composition according to claim 26 in the form of an oral dosage unit or parenteral dosage unit.

28. The pharmaceutical composition according to claim 27, wherein said dosage unit comprises from about 1 mg to about 100 mg of the compound.

\* \* \* \* \*